(12) United States Patent
Yarosh et al.

(10) Patent No.: US 9,283,166 B2
(45) Date of Patent: Mar. 15, 2016

(54) MODULATION OF MELANOGENESIS BY MODIFICATION OF TYROSINASE BY PALMITOYLATION

(71) Applicant: ELC Management LLC, Melville, NY (US)

(72) Inventors: Daniel B. Yarosh, Merrick, NY (US); Lieve Declercq, Ekeren (BE); Yoko Niki, Kakogawa (JP); Naoaki Saito, Kakogawa (JP)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

(21) Appl. No.: 14/675,247

(22) Filed: Mar. 31, 2015

(65) Prior Publication Data

US 2015/0283104 A1 Oct. 8, 2015

Related U.S. Application Data

(62) Division of application No. 14/104,412, filed on Dec. 12, 2013, now abandoned.

(60) Provisional application No. 61/740,048, filed on Dec. 20, 2012.

(51) Int. Cl.

| | | |
|---|---|---|
| *A61K 31/20* | (2006.01) | |
| *A61K 8/00* | (2006.01) | |
| *A61K 8/66* | (2006.01) | |
| *A61K 8/64* | (2006.01) | |
| *A61Q 19/02* | (2006.01) | |
| *A61Q 5/10* | (2006.01) | |
| *A61K 8/36* | (2006.01) | |
| *A61Q 5/08* | (2006.01) | |
| *A61Q 17/04* | (2006.01) | |
| *A61K 45/06* | (2006.01) | |

(52) U.S. Cl.
CPC . *A61K 8/66* (2013.01); *A61K 8/361* (2013.01); *A61K 8/64* (2013.01); *A61K 31/20* (2013.01); *A61K 45/06* (2013.01); *A61Q 5/08* (2013.01); *A61Q 5/10* (2013.01); *A61Q 17/04* (2013.01); *A61Q 19/02* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 5,714,516 | A | 2/1998 | Harper et al. |
| 6,890,954 | B1 * | 5/2005 | Resh ............... A61K 31/20 514/558 |
| 2003/0153619 | A1 | 8/2003 | Hwang et al. |
| 2008/0254055 | A1 | 10/2008 | Oblong et al. |
| 2010/0183527 | A1 | 7/2010 | Moser et al. |
| 2011/0044920 | A1 | 2/2011 | Hines et al. |
| 2012/0021029 | A1 | 1/2012 | Garcia Sanz et al. |

OTHER PUBLICATIONS

Aicart-Ramos, C. et al., Protein palmitoylation and subcellular trafficking; Biochimica et Biophysica Acta 1808 (2011) 2981-2994.
Cho, S. et al., Antisense palmitoyl protein thioesterase 1 (PPT1) treatment inhibits PPT1 activity and increases cell death in LA-N-5 neuroblastoma cells; J Neurosci Res. Oct. 15, 2000;62(2):234-40.
Dawson, G. et al., Palmitoyl:protein thioesterase (PPT1) inhibitors can act as pharmacological chaperones in infantile Batten Disease; Biochem Biophys Res Commun. Apr. 23, 2010; 395(1): 66-69.
Ganesan AK, et al. (2008) Genome-Wide siRNA-Based Functional Genomics of Pigmentation Identifies Novel Genes and Pathways That Impact Melanogenesis in Human Cells. PLoS Genet 4(12): e1000298. doi:10.1371/journal.pgen.1000298. Dec. 5, 2008.
International Search Report of PCT-US2013-074666 (Mar. 25, 2014).
Iwanaga, T. et al., Dynamic protein palmitoylation in cellular signaling; Prog. Lipid Res., May-Jul. 2009;48(3-4);117-27.
Meng, L. et al., The antiproliferative agent Didemnin B uncompetitively inhibits palmitoyl protein thioesterase; Biochem. 1998, vol. 37, No. 29, pp. 10488-10492.
Niki, Y. et al., "Regulation of melanin synthesis by dsc-palmitoylation of tyrosinase" at The 25th Annual Meeting of the Japanese Society for Pigment Cell Research; abstract publlished in Pigment Cell Melanoma Res. vol. 26, No. 6, Nov. 2013; p. E10.
Salaun, C. et al., The intracellular dynamic of protein palmitoylation; J. Cell Biol. vol. 191 No. 7, 2010 pp. 1229-1238.
Tsutsumi, R. et al., Discovery of protein-palmitoylating enzymes; Pflugers Arch. Sep. 2008; 456(6): 1199-1201.
Written Opinion of the ISA for PCT-US2013-074666 (Mar. 25, 2014).
Wu, et al., Melanoregulin is stably targeted to the melanosome membrane by palmitoylation; Biochem Biophys Res Commun. Sep. 21, 2012; 426(2): 209-214.

* cited by examiner

*Primary Examiner* — Nannette Holloman
(74) *Attorney, Agent, or Firm* — Cynthia R. Miller

(57) ABSTRACT

Compositions and methods for modulating melanogenesis by modifying tyrosinase palmitoylation are provided.

3 Claims, 19 Drawing Sheets

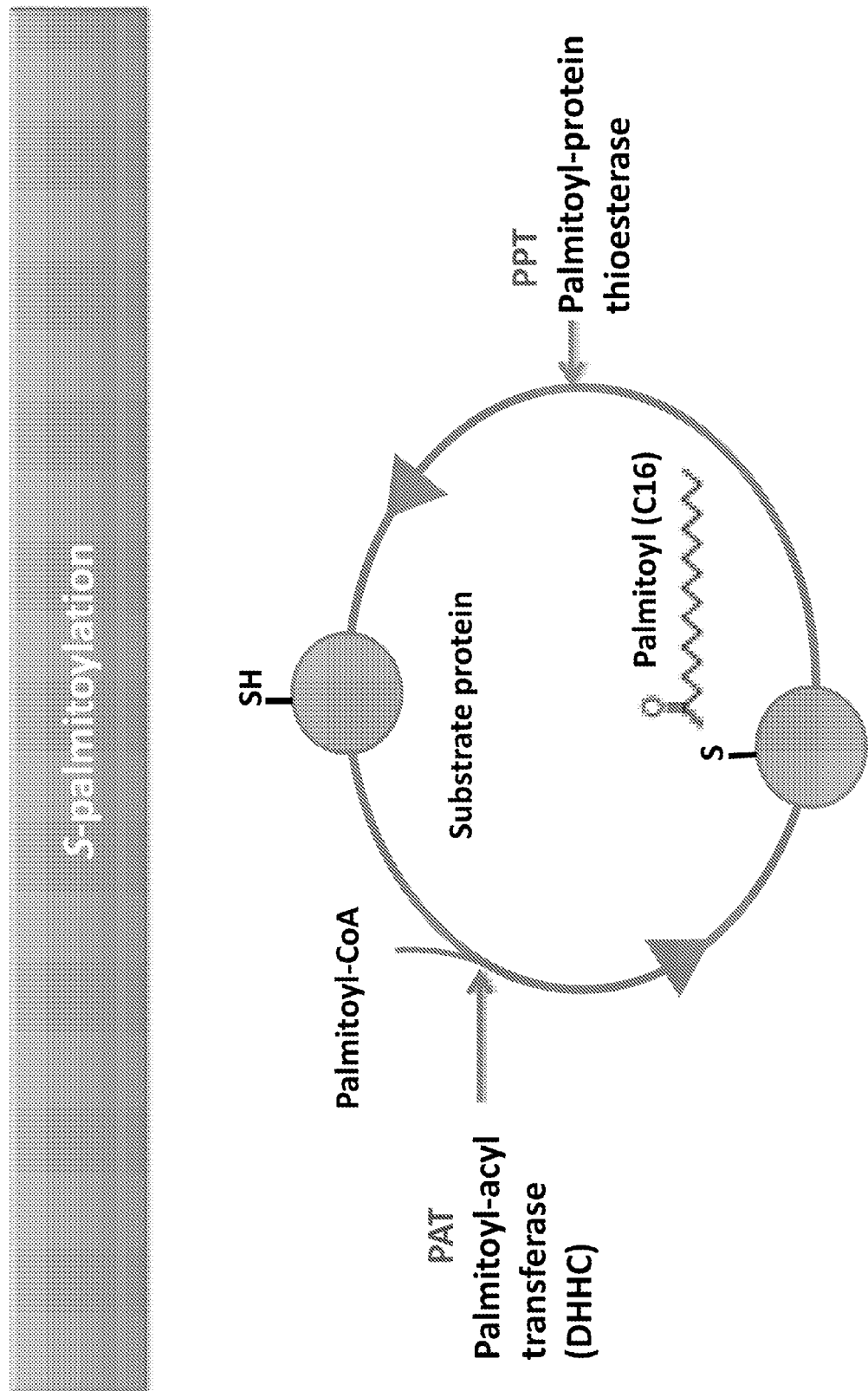
Fig.1 The cycle of protein palmitoylation. S-palmitoylation is the addition of palmitic acid (C16) to specific cysteine residue through a thioester and is the only reversible lipid modification.

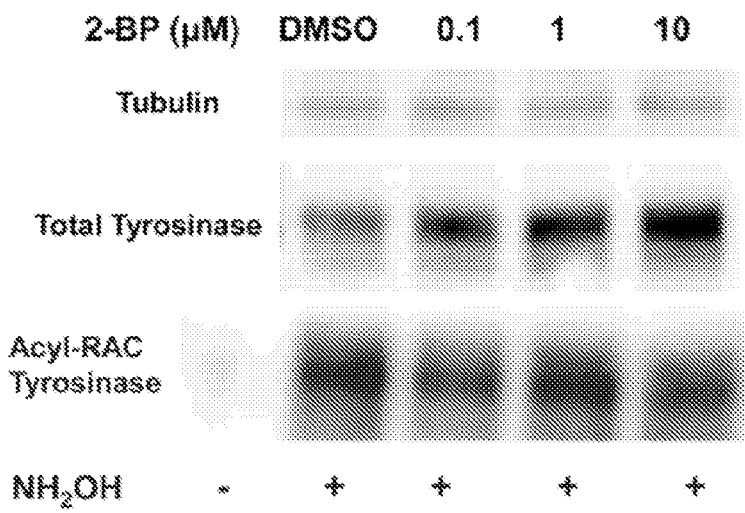
Fig.2A Effect of palmitoylation inhibitor (2-BP) on palmitoylation of tyrosinase.
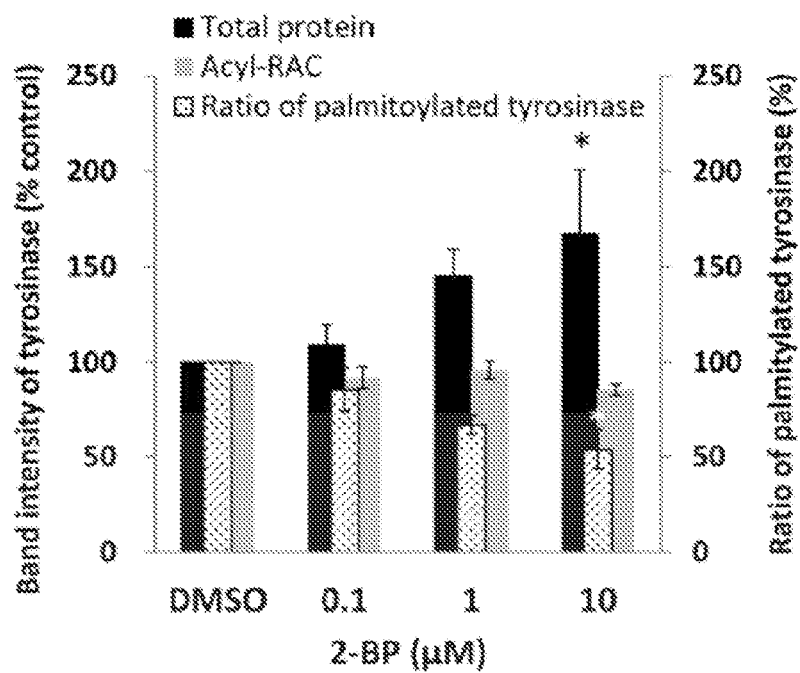
Fig.2B Effect of palmitoylation inhibitor (2-BP) on palmitoylation of tyrosinase.

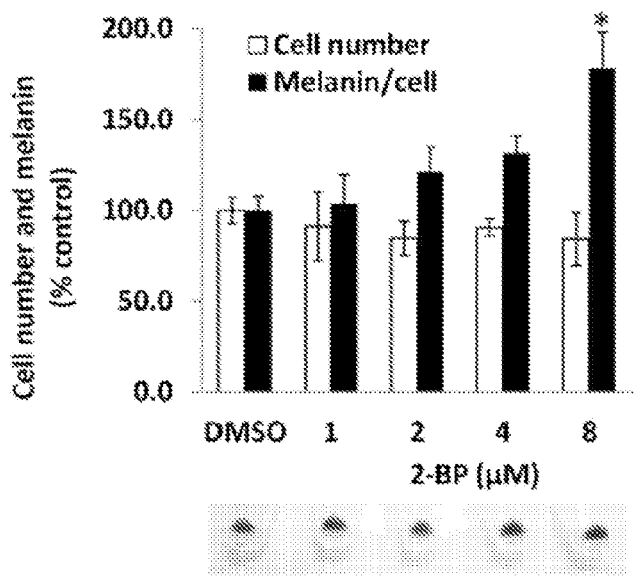
Fig.3A Effect of 2-BP on melanin synthesis in NHEM and reconstructed human skin model.
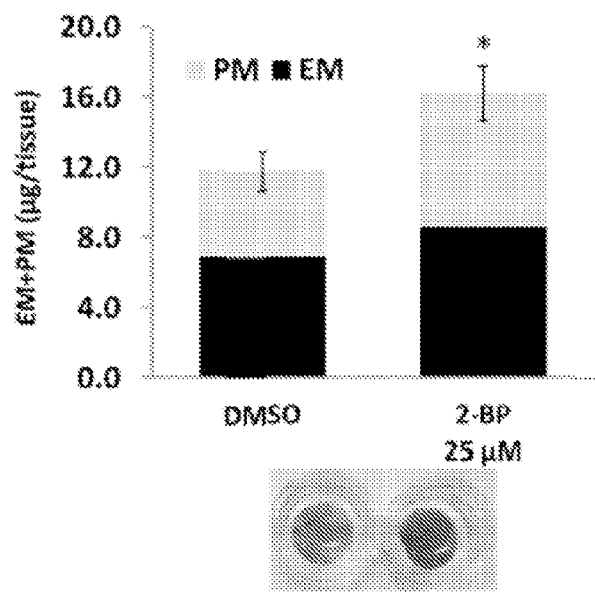
Fig.3B Effect of 2-BP on melanin synthesis in NHEM and reconstructed human skin model.

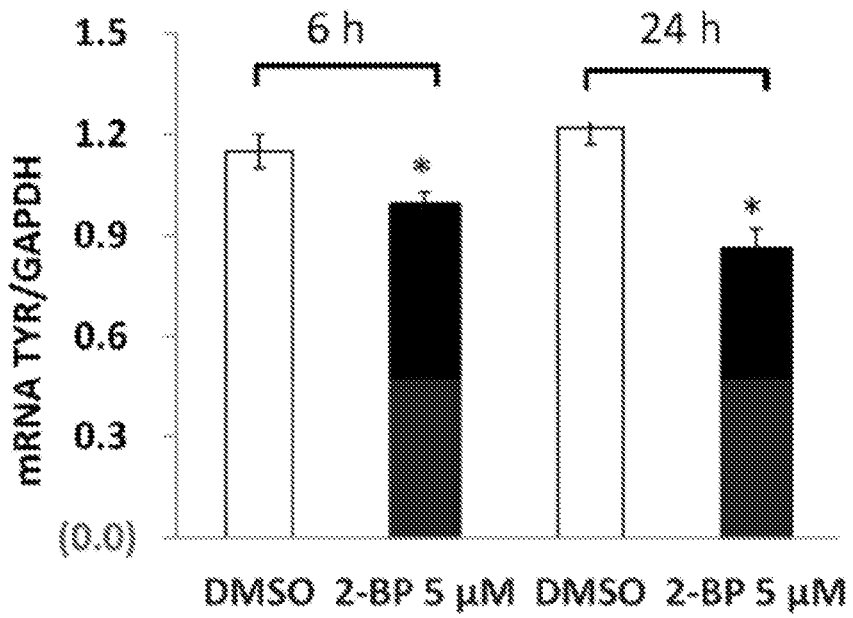
Fig.4A Effect of 2-BP on mRNA expression and glycosylation of tyrosinase.
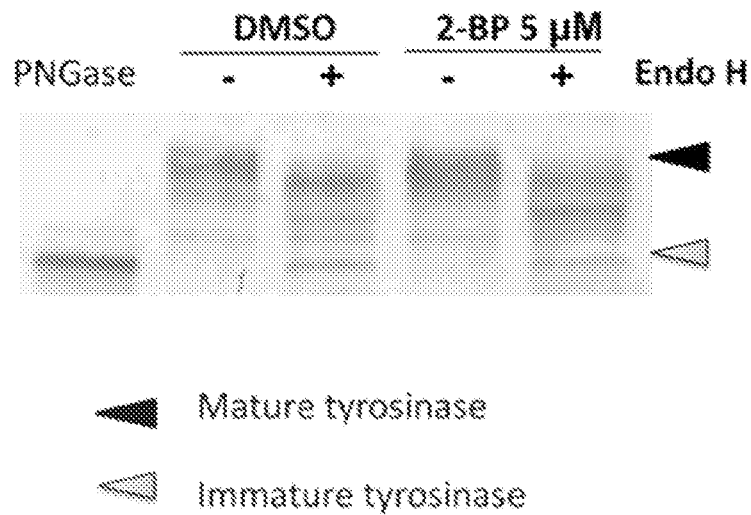
Fig.4B Effect of 2-BP on mRNA expression and glycosylation of tyrosinase.

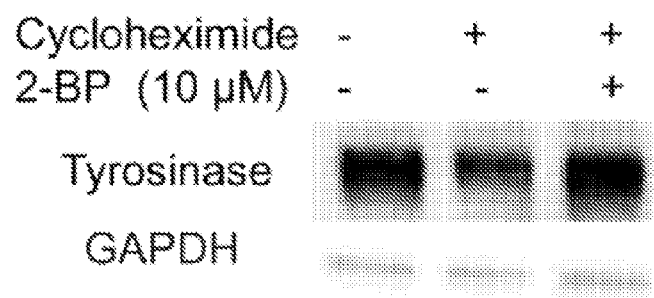
Fig.5A Effect of 2-BP on degradation of tyrosinase.
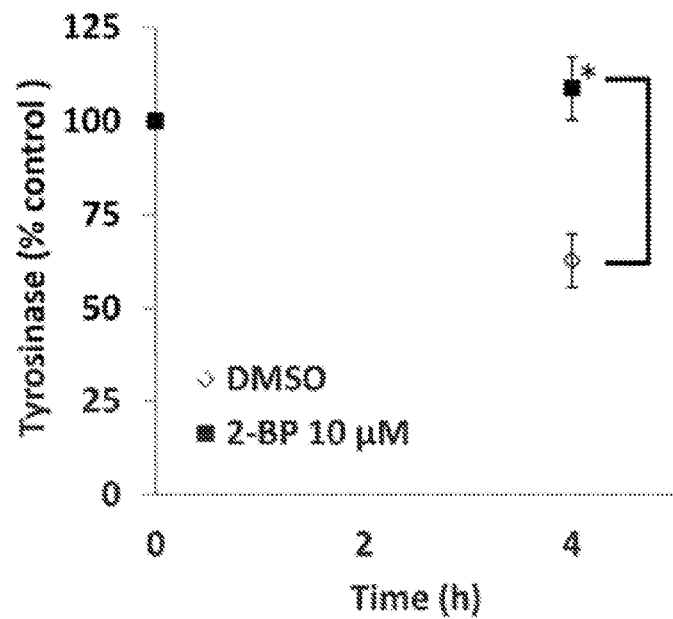
Fig.5B Effect of 2-BP on degradation of tyrosinase.

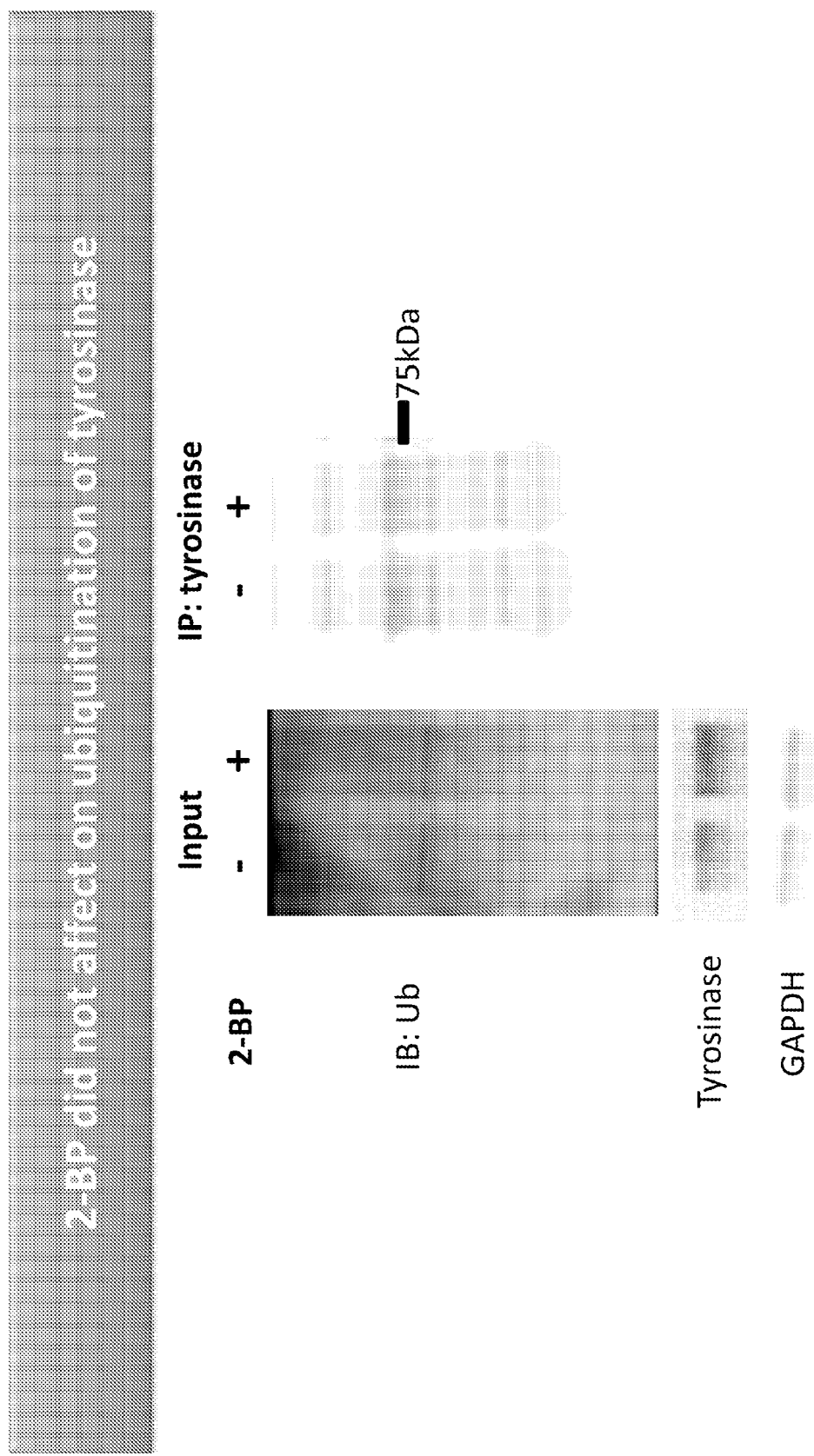
Fig.6 Effect of 2-BP on ubiquitination of tyrosinase.

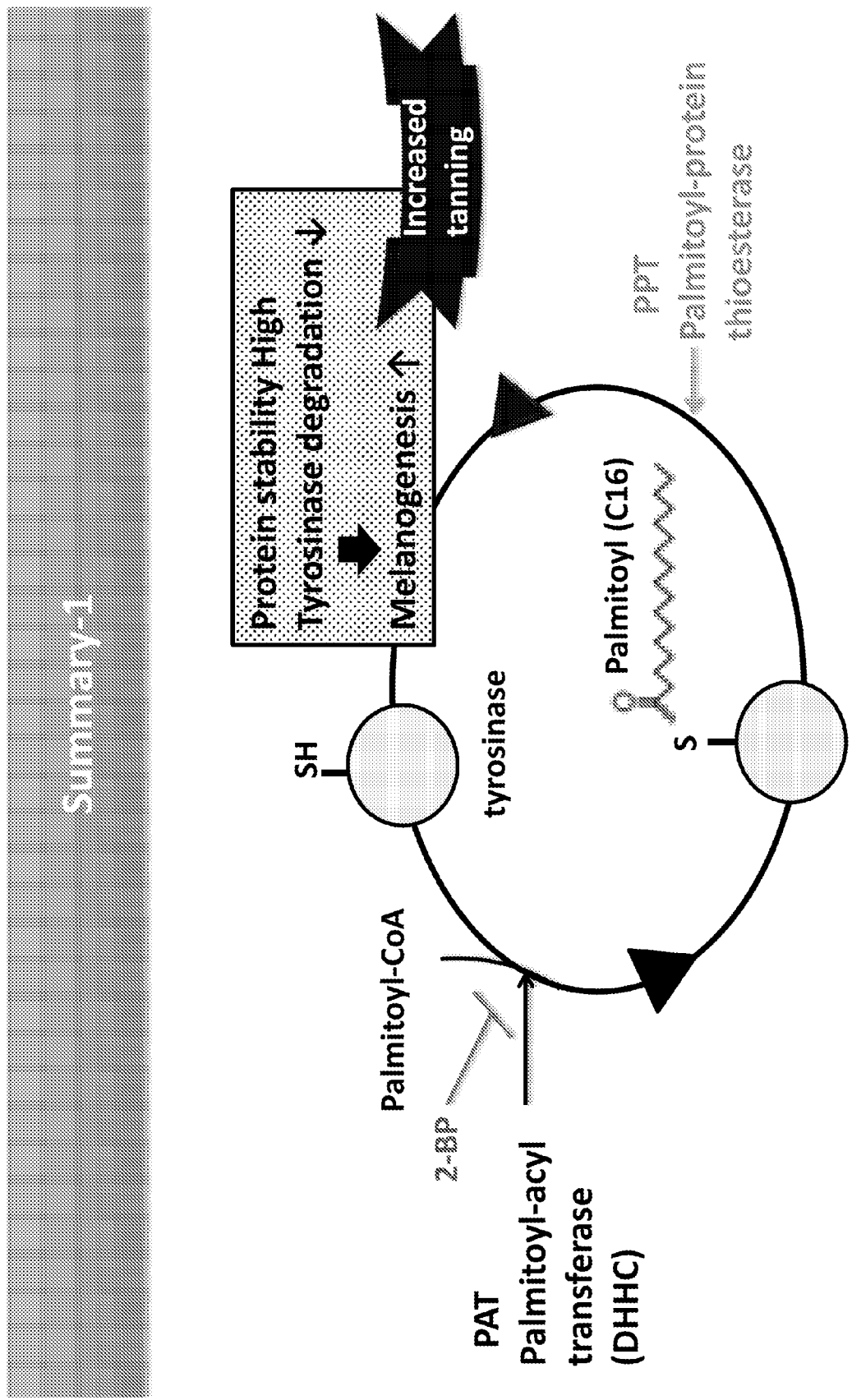
Fig.7 Effect of 2-BP.

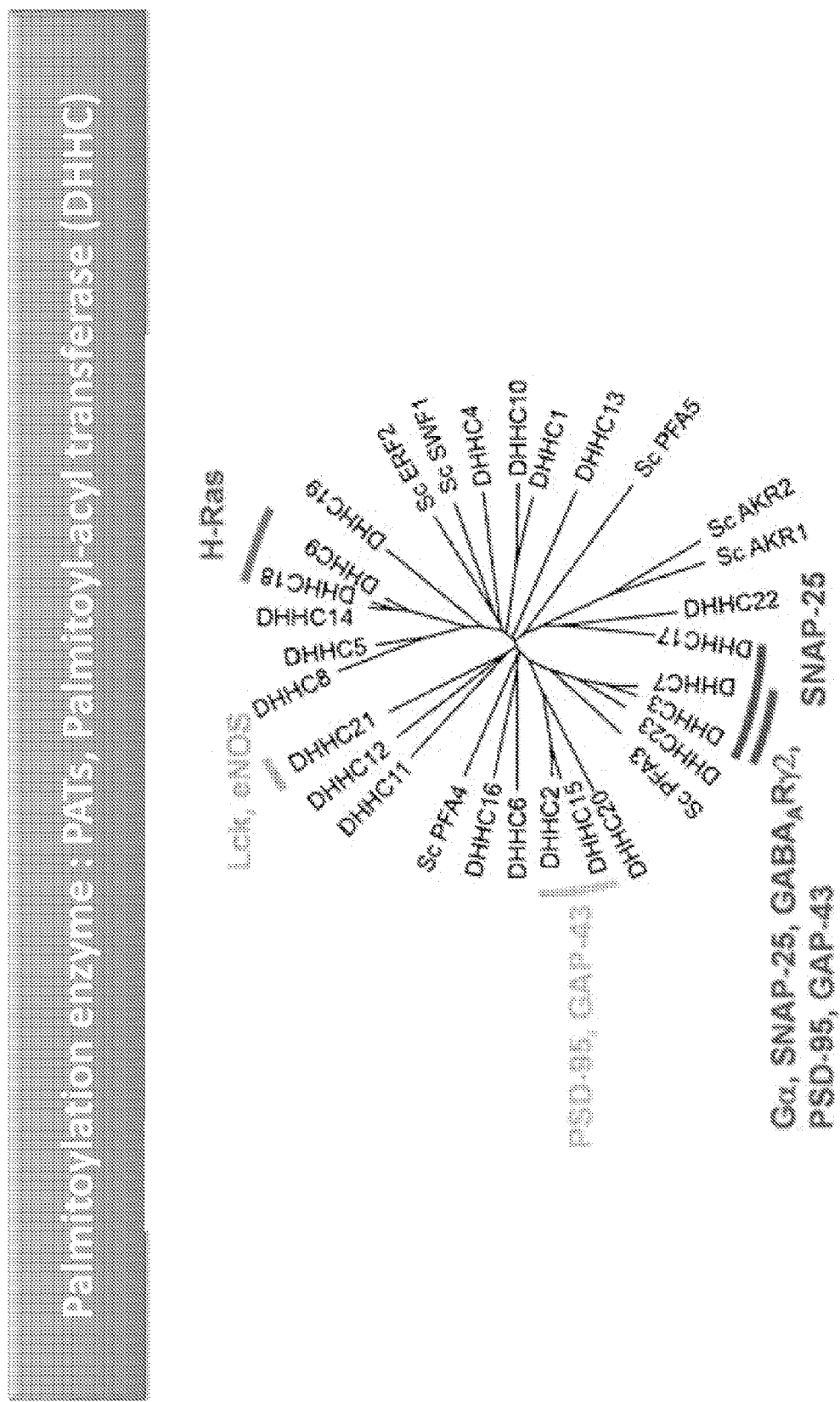
Fig.8 Palmitoylation enzymes.

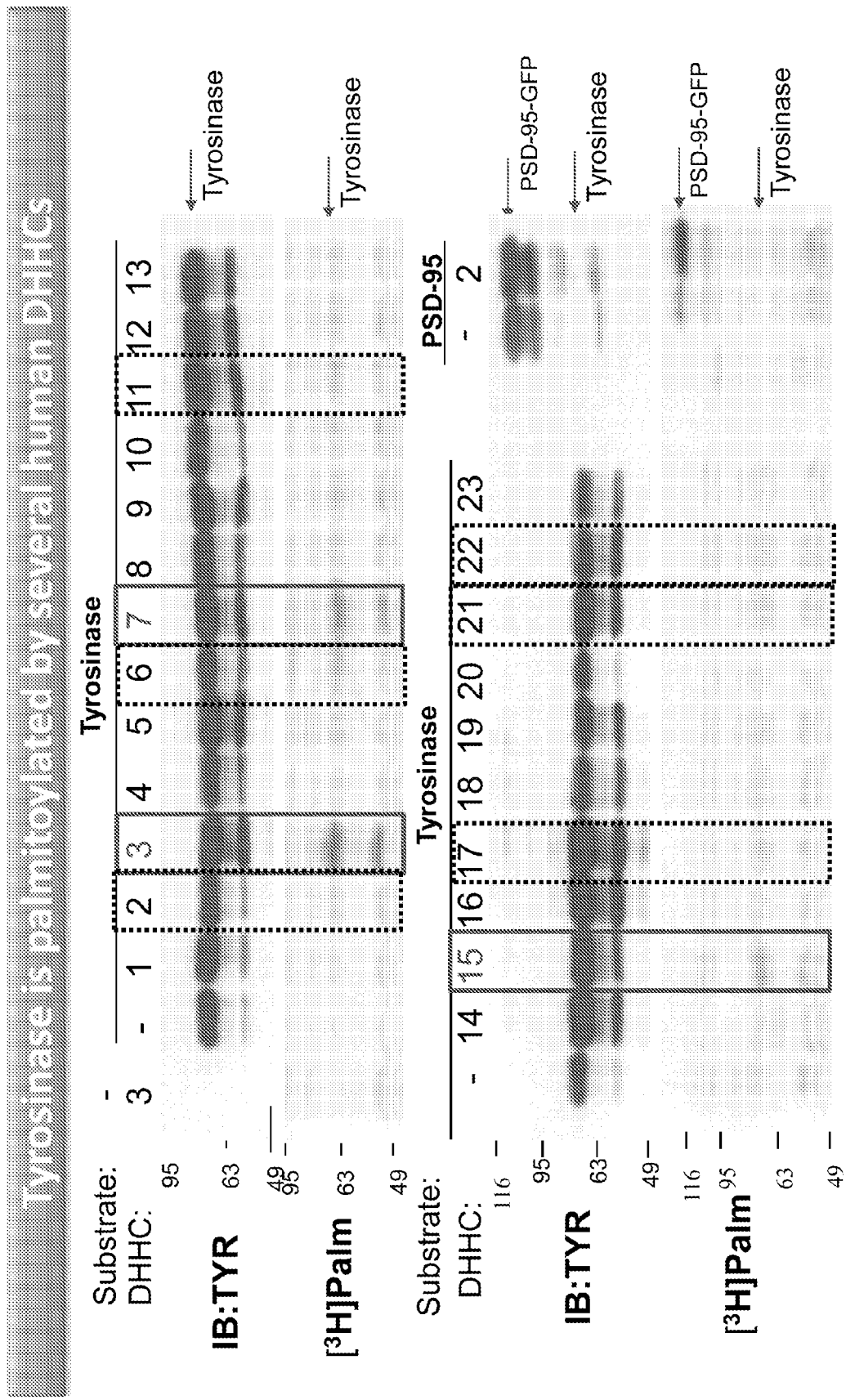
Fig. 9 Screening of tyrosinase specific DHHC.

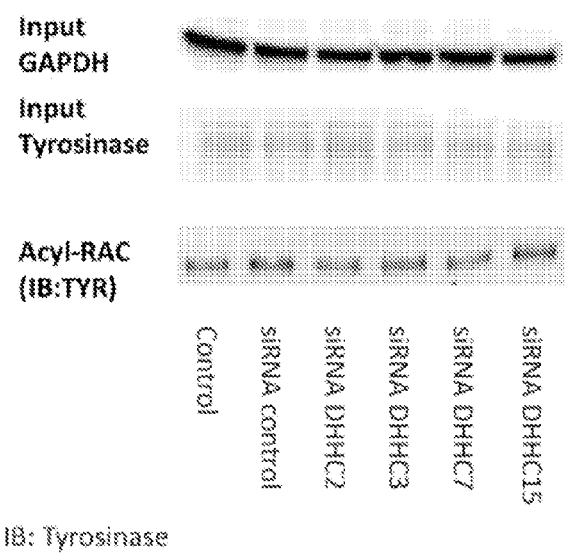
Fig.10A Effect of DHHC3,7, 2 and 15 silencing on tyrosinase palmitoylation in MNT-1 cell.
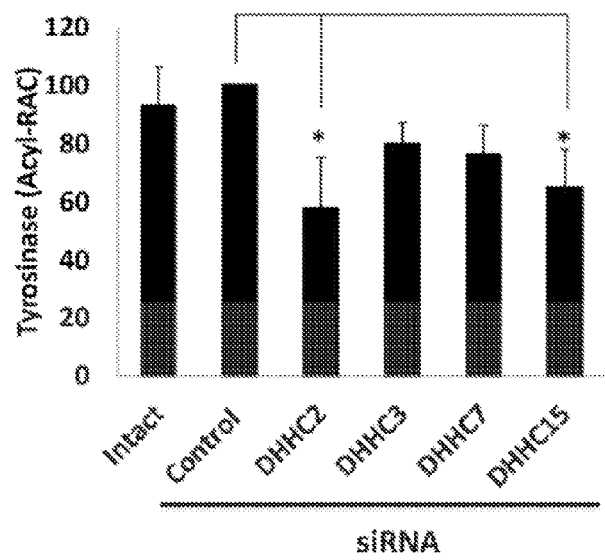
Fig.10B Effect of DHHC3,7, 2 and 15 silencing on tyrosinase palmitoylation in MNT-1 cell.

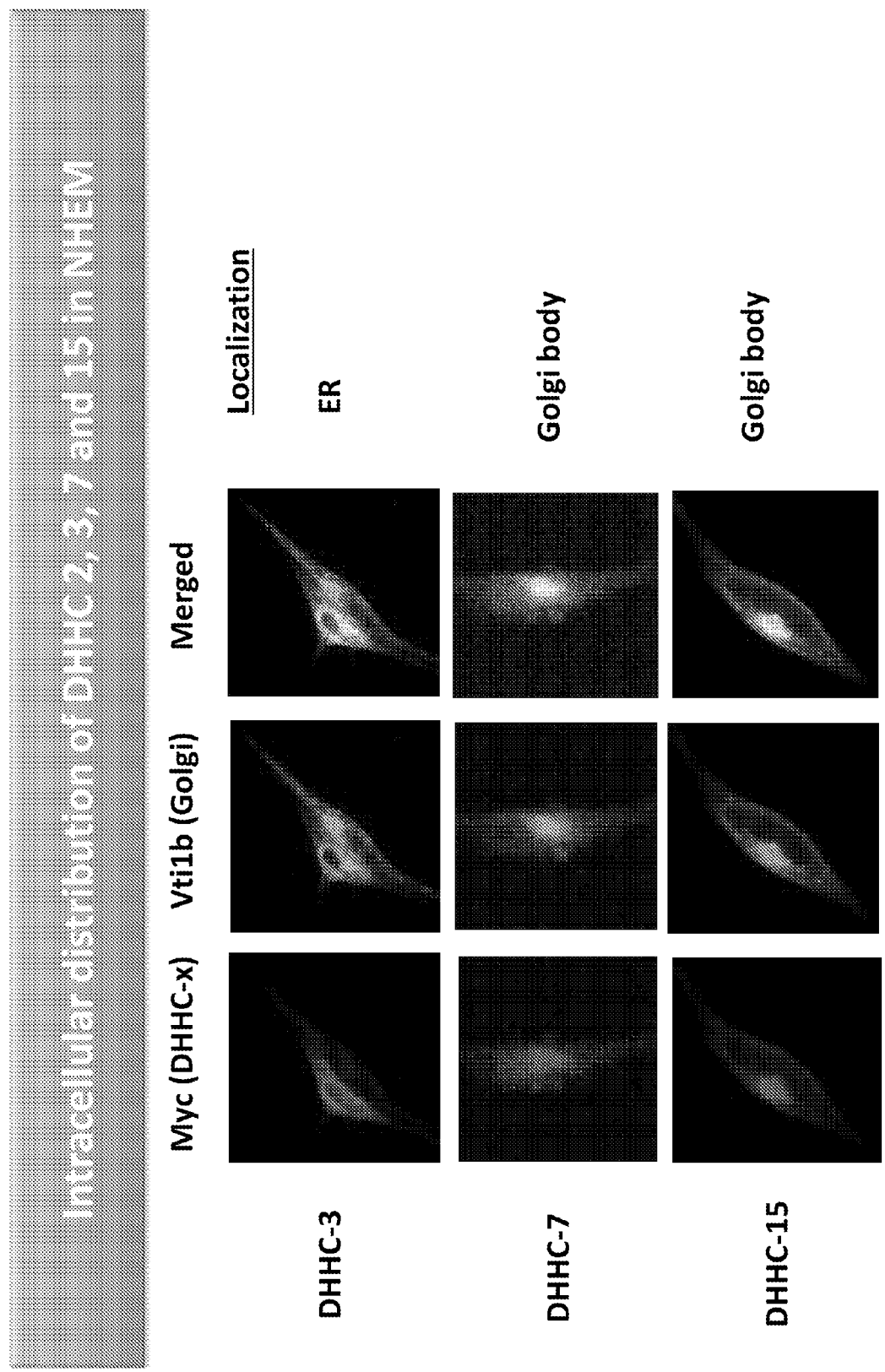
Fig.11A Analysis of the intracellular localizations of DHHC2, 3, 7 and 15-myc in NHEM.

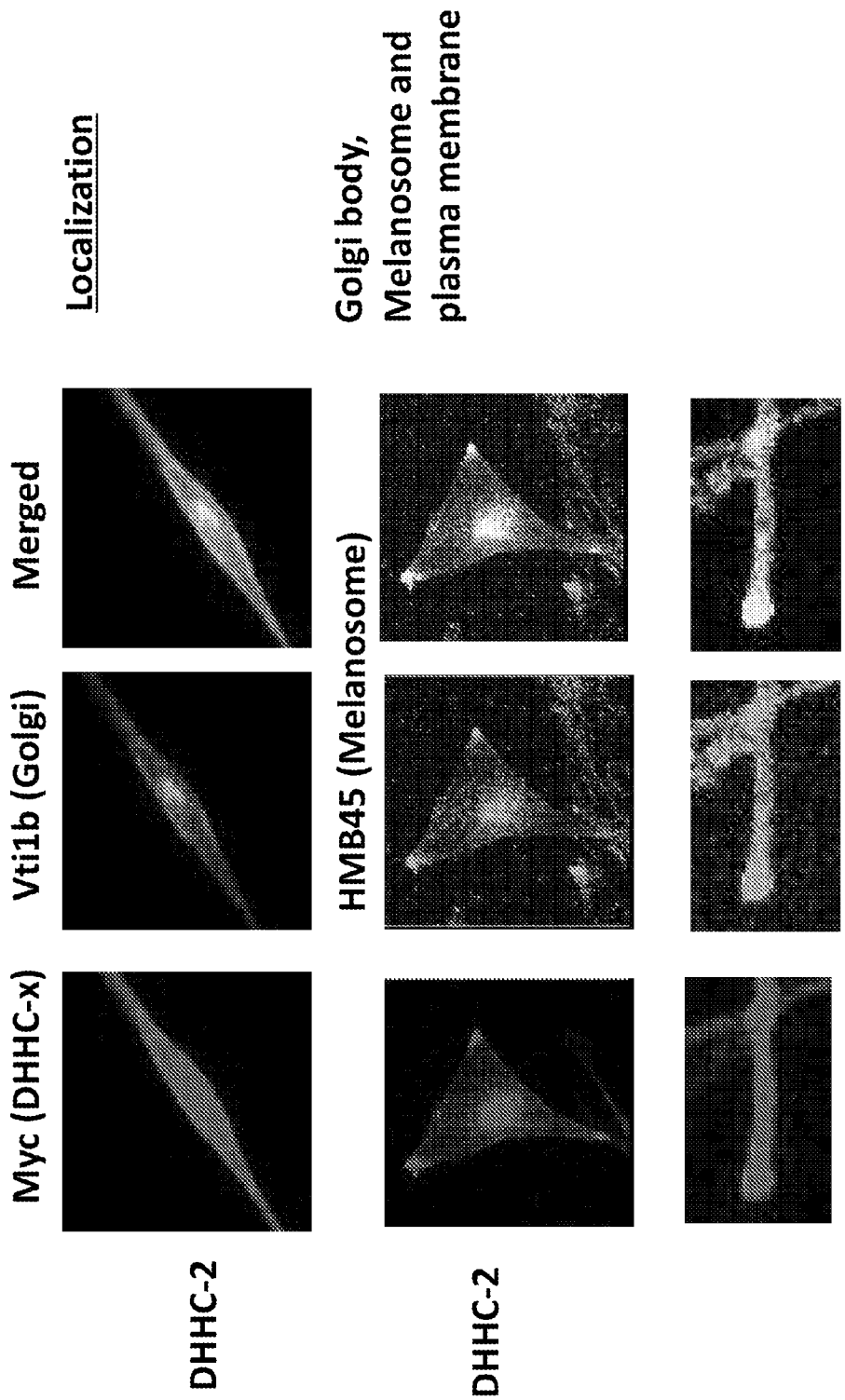
Fig.11B  Analysis of the intracellular localizations of DHHC2, 3, 7 and 15-myc in NHEM.

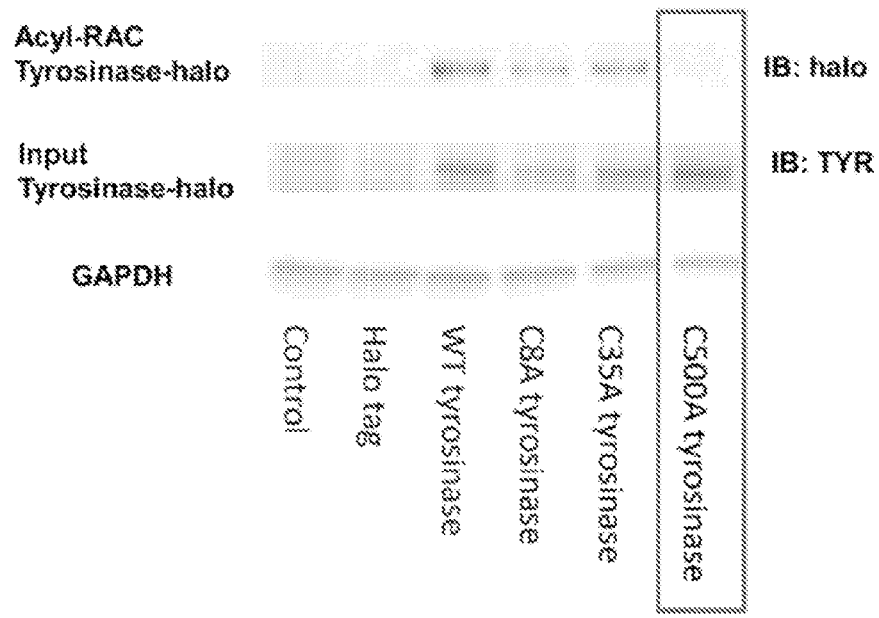
Fig.12A Palmitoylation site in human tyrosinase.
| Position of cysteine | Score |
|---|---|
| 8 | 0.976 |
| 35 | 0.676 |
| 500 | 1.3 |
Fig.12B Palmitoylation site in human tyrosinase.

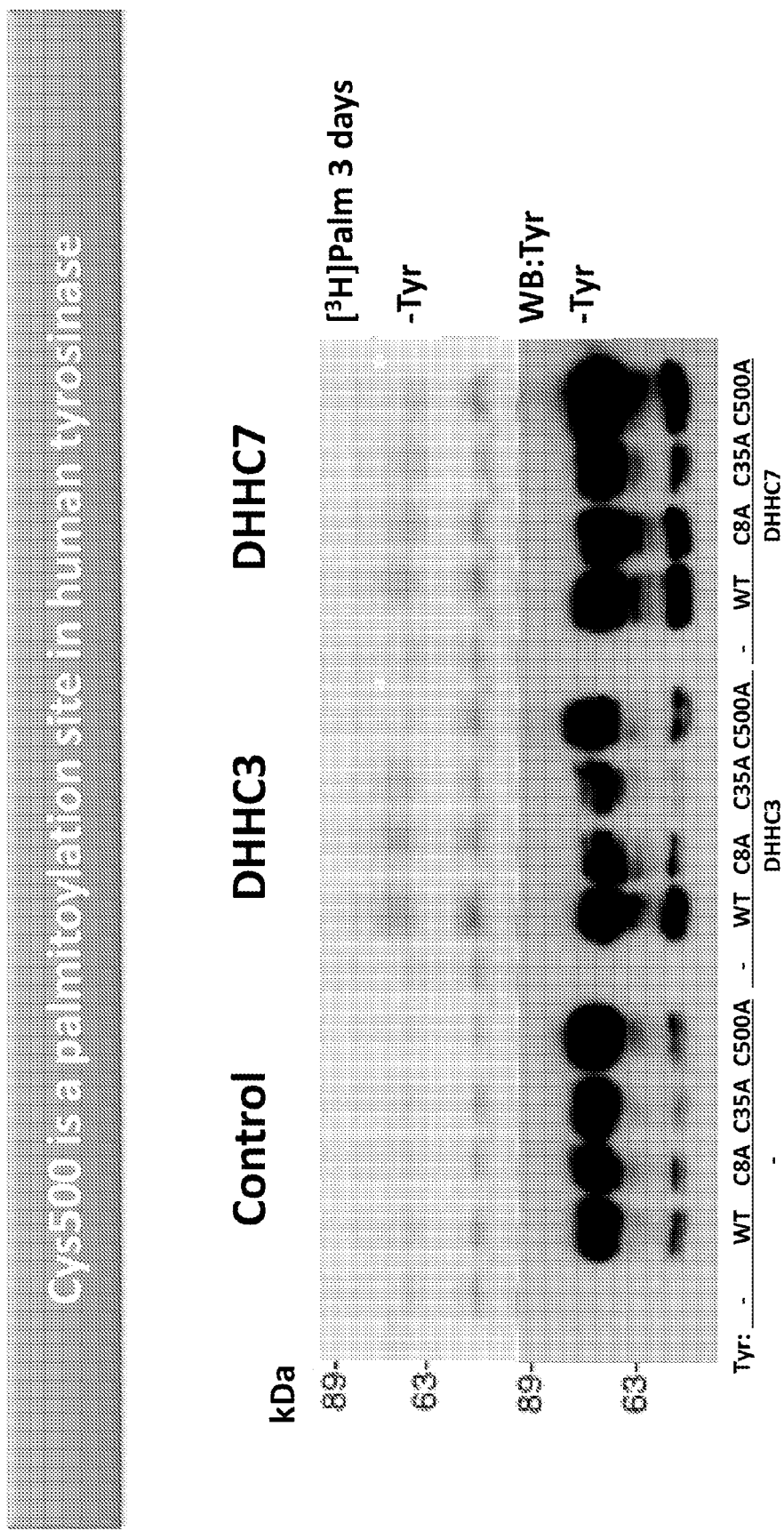
Fig.13A Palmitoylation site in human tyrosinase.

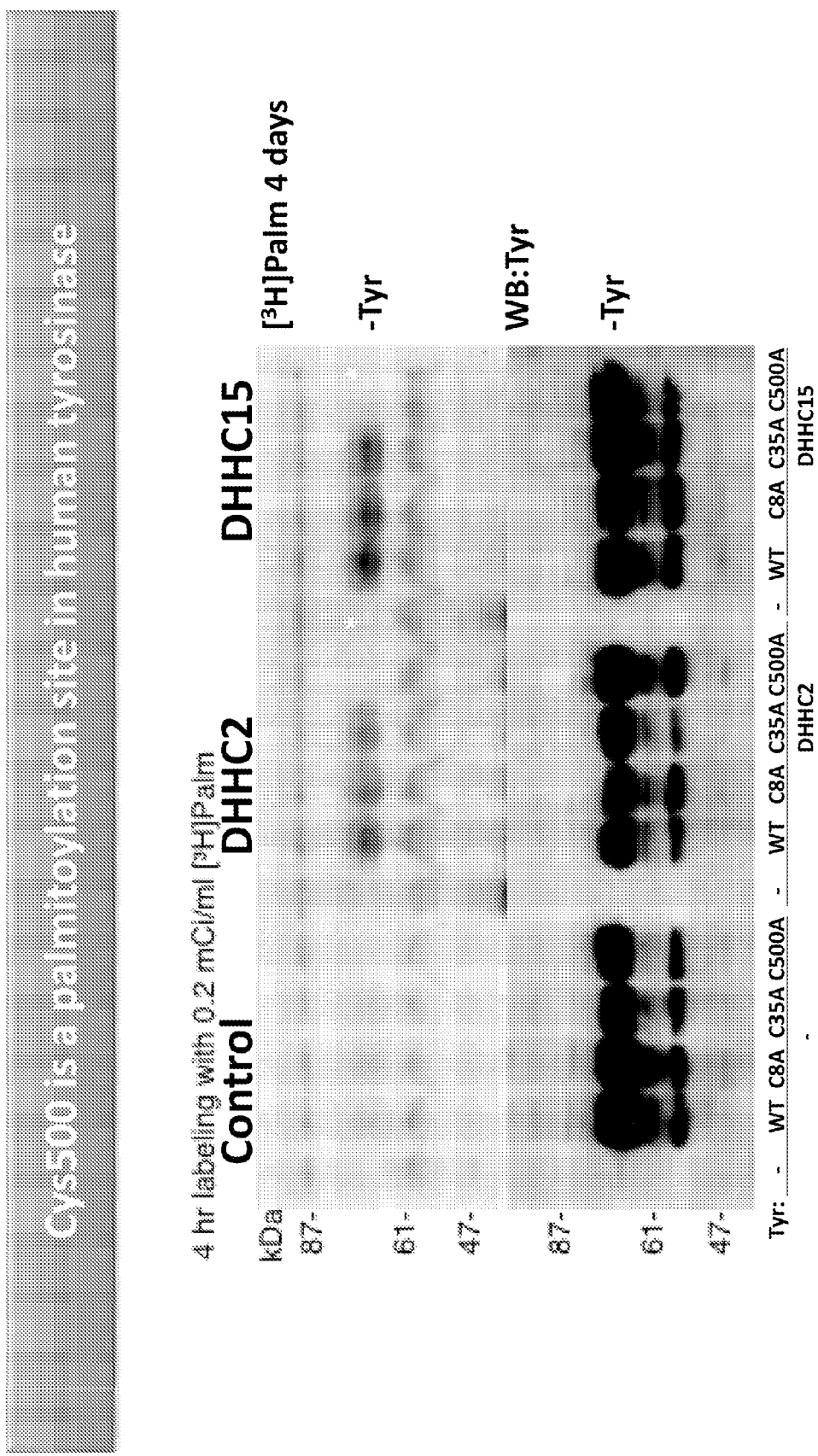
Fig.13B Palmitoylation site in human tyrosinase.

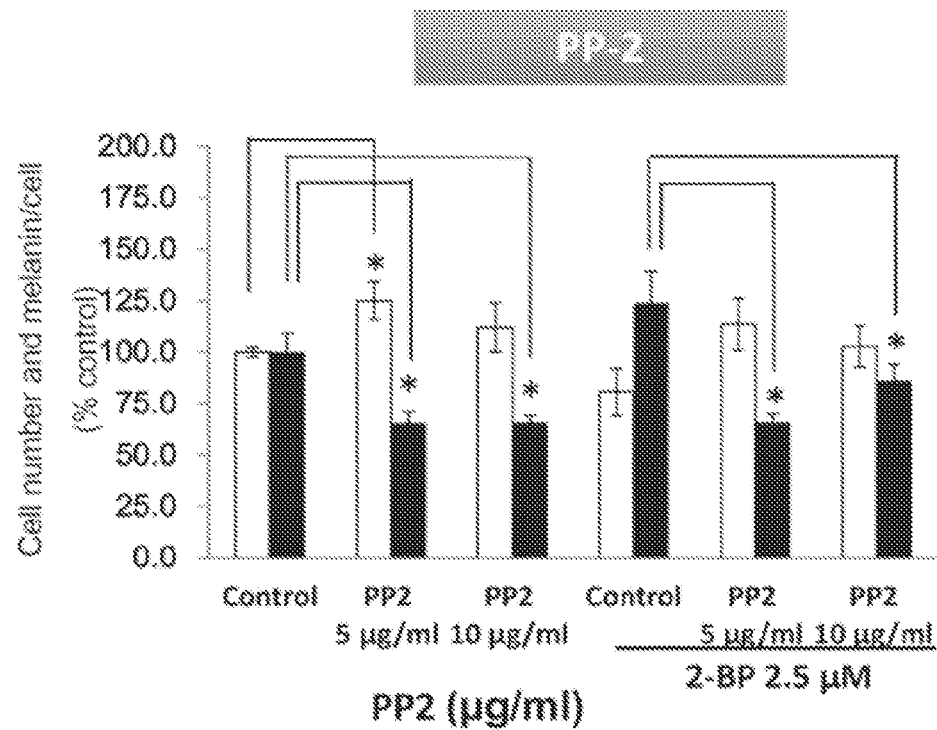
Fig.14A Effect of PP-2 and KA on melanin synthesis in NHEM.
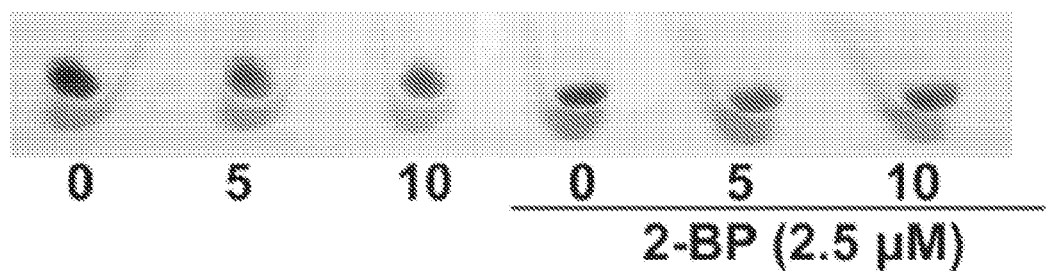
Fig.14B Effect of PP-2 and KA on melanin synthesis in NHEM.

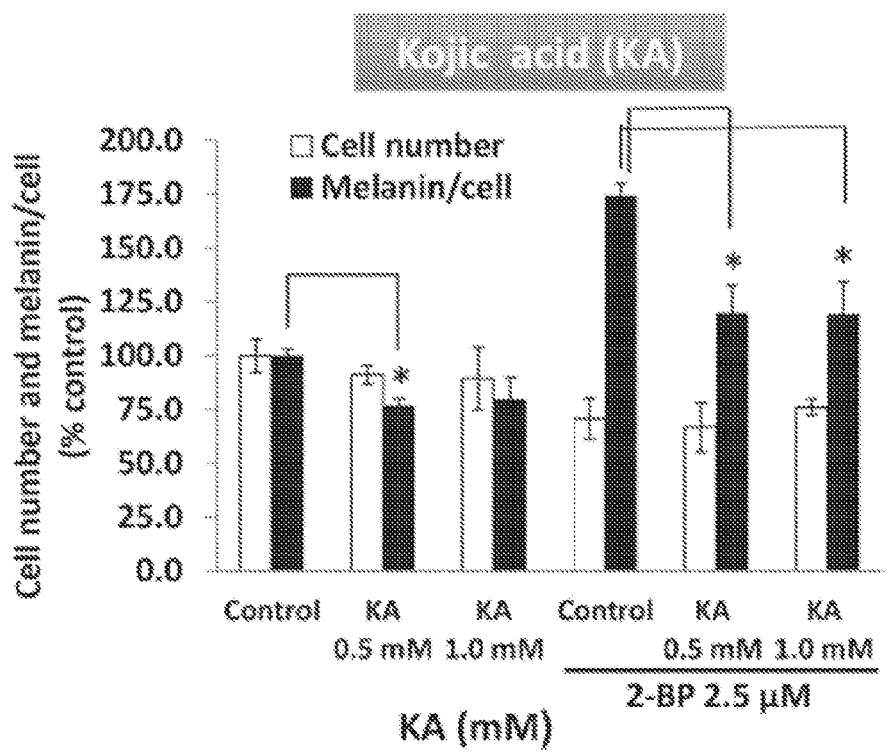
Fig.14C Effect of PP-2 and KA on melanin synthesis in NHEM.
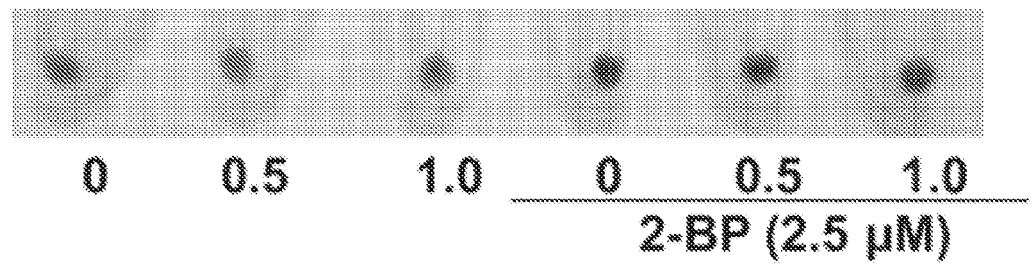
Fig.14D Effect of PP-2 and KA on melanin synthesis in NHEM.

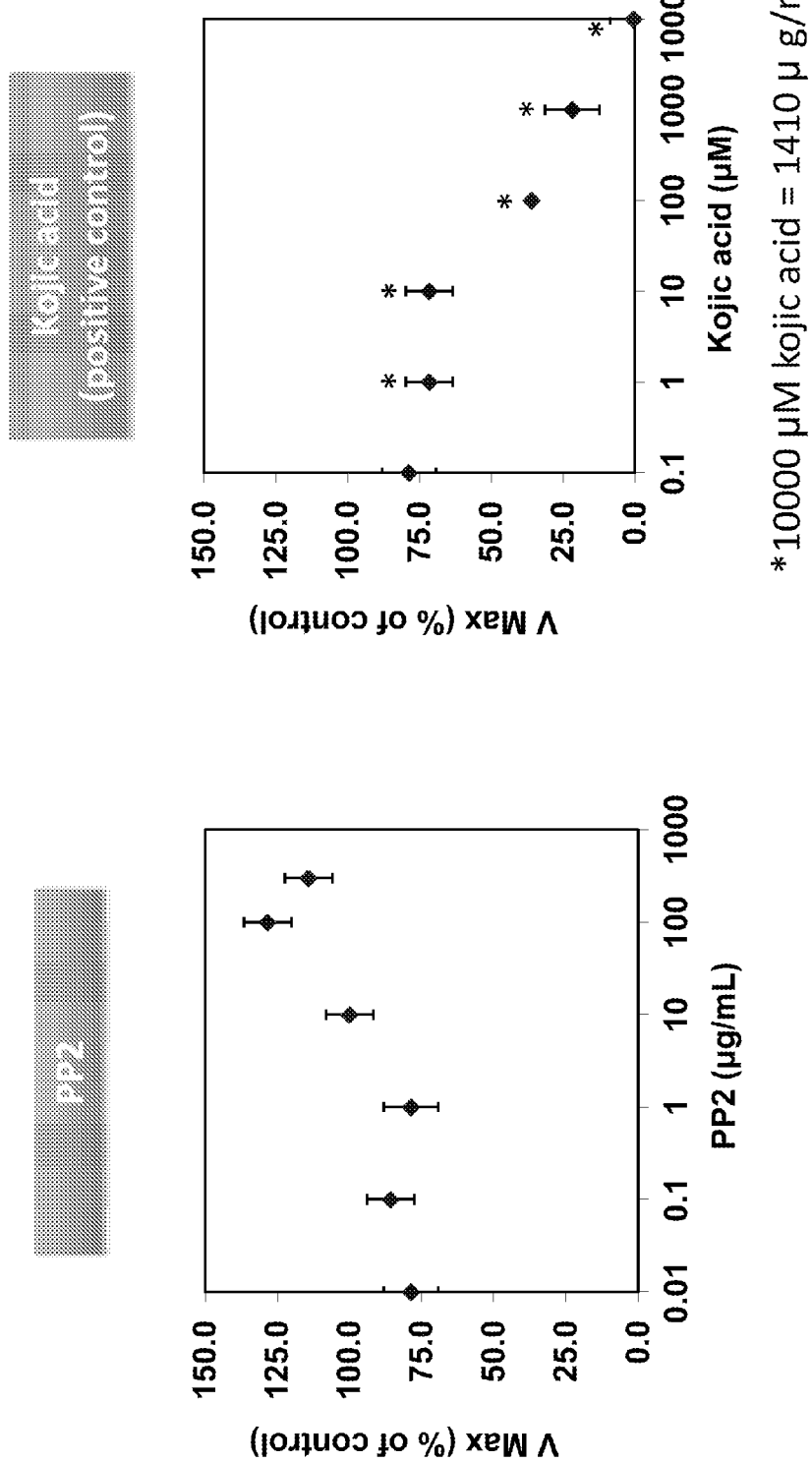
Fig.15 Effect of PP-2 and KA on human tyrosinase (DOPA oxidation) activity in vitro.

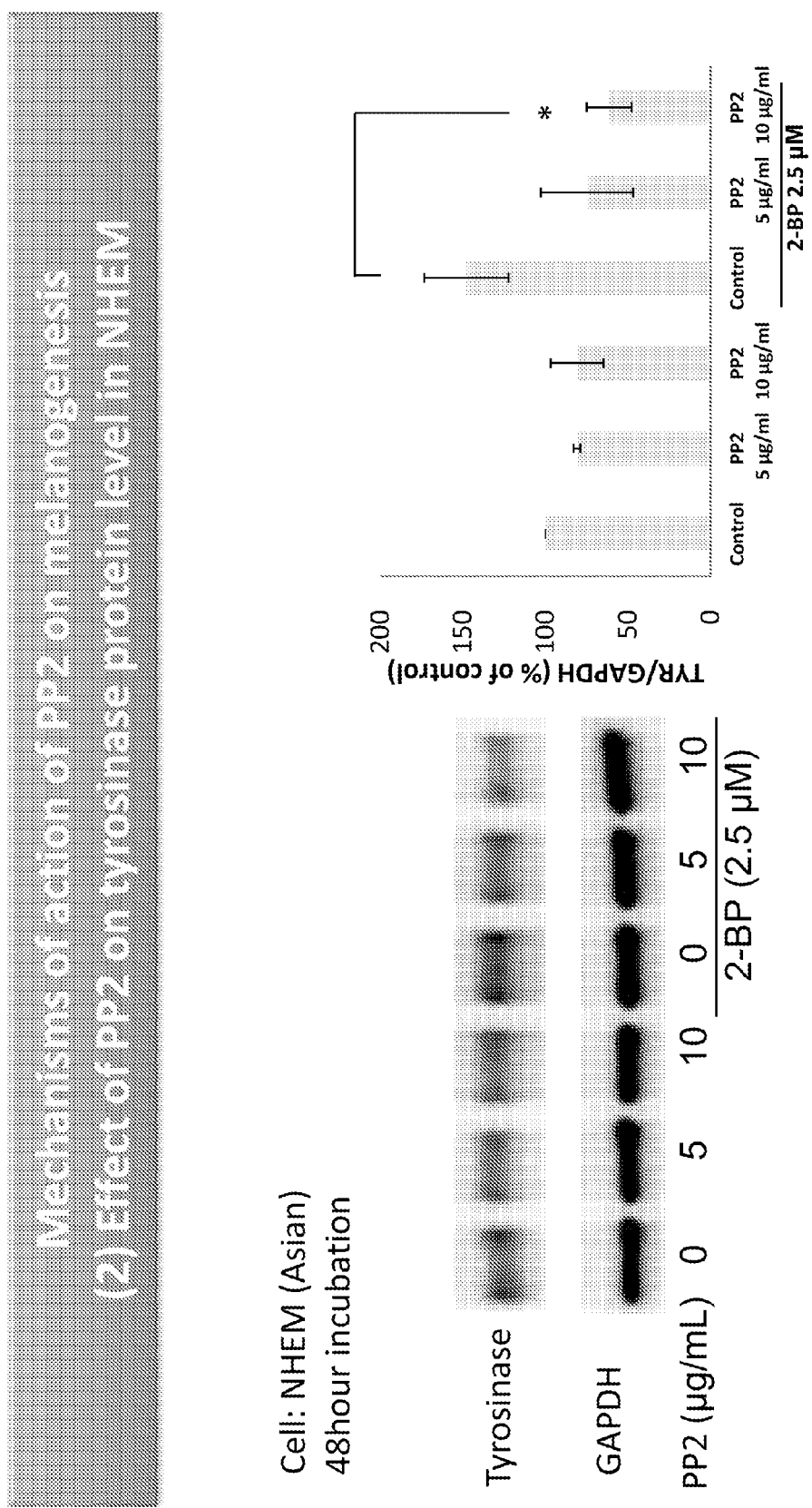
Fig.16 Effect of PP-2 on tyrosinase protein in NHEM.

MODULATION OF MELANOGENESIS BY MODIFICATION OF TYROSINASE BY PALMITOYLATION

CROSS-REFERENCE TO RELATED APPLICATIONS

This application is a divisional of U.S. Ser. No. 14/104,412, filed Dec. 12, 2013, which claims priority to U.S. Provisional Patent Application No. 61/740,048, filed Dec. 20, 2012.

BACKGROUND OF THE INVENTION

1. Field of the Invention

The invention relates to the regulation of melanin synthesis. More specifically, the invention is concerned with compositions and methods which modify the activity of tyrosinase.

2. Description of the Prior Art

Pigmentation of human skin and hair is a concern for people around in the world. In some cases the desire is to have an overall lighter complexion. Most generally people wish to have even skin tone regardless of the underlying color. All people wish to delay the appearance of grey hair, which is a sign of aging.

Pigmentation of skin and hair is controlled by the specialized cell called a melanocyte. The melanocyte contains within it an organelle called a melanosome which manufactures the forms of melanin (including black eumelanin and red pheomelanin) and then the melanocyte distributes it within the skin or hair. The most important enzyme in the biosynthesis of melanin is tyrosinase, and its inhibition has been the focus of most commercial products that are designed to lighten skin color.

Tyrosinase is a metalloprotein that is synthesized at ribosomes, trafficked through the Golgi apparatus to a pre-melanosome, and then loaded into it. As the pre-melanosome matures, copper molecules are also loaded into it as co-factors for the tyrosinase, and the pH is increased to reach the optimum for the enzyme. The mature melanosome then begins synthesizing melanin.

The trafficking of tyrosinase is not well understood. Recently, palmitoylation of proteins has received attention as a mechanism of subcellular localization of mammalian proteins (reviewed in T. Iwanaga, R. Tsutsumi, J. Noritake, Y. Fukata, M. Fukata "Dynamic protein palmitoylation in cellular signaling, *Progress in Lipid Research* 48:117-127, 2009; C. Salaun, J. Greaves, L. Chamberlain "The intracellular dynamic of protein palmitoylation" *J. Cell Biol.* 191: 1229-1238, 2010; C. Aicart-Ramos, R. Valero, I. Rodrigues-Crespo "Protein palmitoylation and subcellular trafficking" *Bioch. Biophys. Acta* 1808:2981-2994. 2011). Tyrosinase is not disclosed as a target of palmitoylation in any of these reviews.

BRIEF SUMMARY OF THE INVENTION

In accordance with one aspect of the invention, a method for increasing the appearance of melanin in mammalian skin or hair in need of such increase, comprising treating the skin or hair with one or more inhibitors of DHHC 2, 3, 7, 15, 6, 11, 17, 21, or 22 is provided.

In accordance with a second aspect of the invention, a method for reducing the appearance of melanin in mammalian skin or hair in need of such reduction by treating the skin or hair with one or more inhibitors of PPT-type enzymes is provided.

In accordance with a third aspect of the invention, a method is provided for reducing the appearance of melanin in mammalian skin or hair in need of such reduction by treating the skin or hair with at least one palmitoylated peptide.

In accordance with a fourth aspect of the invention, a cosmetic or dermatological composition for increasing the appearance of melanin in mammalian skin or hair, comprising a melanin increasing-effective amount of one or more inhibitors of DHHC 2, 3, 7, 15, 6, 11, 17, 21, or 22, in a cosmetically or dermatologically acceptable vehicle is provided.

In accordance with a fifth aspect of the invention, there is provided a cosmetic or dermatological composition for reducing the appearance of melanin in mammalian skin or hair, comprising a melanin reducing-effective amount of one or more inhibitors of PPT-type enzymes in a cosmetically or dermatologically acceptable vehicle.

In accordance with a sixth aspect of the invention, a cosmetic or dermatological composition for reducing the appearance of melanin in mammalian skin or hair comprising a melanin reducing-effective amount of at least one palmitoylated peptide in a cosmetically or dermatologically acceptable vehicle is provided.

Other aspects and objectives of the present invention will become more apparent from the ensuing description and claims.

BRIEF DESCRIPTION OF THE DRAWINGS

FIG. 1 is a schematic representation of the cycle of protein palmitoylation.

FIGS. 2A and 2B depict the effect of palmitoylation inhibitor (2-BP) on palmitoylation of tyrosinase.

FIGS. 3A and 3B represent the effect of 2-BP on melanin synthesis in NHEM and reconstructed human skin model.

FIGS. 4A and 4B illustrate the effect of 2-BP on mRNA expression and glycosylation of tyrosinase.

FIGS. 5A and 5B represent the effect of 2-BP on degradation of tyrosinase.

FIG. 6 depicts the effect of 2-BP on ubiquitination of tyrosinase.

FIG. 7 represents the effect of 2-BP on tyrosinase palmitoylation.

FIG. 8 is an illustration of the DHHC (Palmitoylation) family of proteins.

FIG. 9 represents the results of screening for tyrosinase specific DHHC.

FIGS. 10A and 10B illustrate the effect of DHHC 2, 3, 7 and 15 silencing on tyrosinase palmitoylation in MNT-1 cell.

FIGS. 11A and 11B represent analysis of the intracellular localizations of DHHC 2, 3, 7 and 15-myc in NHEM.

FIGS. 12A and 12B illustrate the Palmitoylation site in human tyrosinase.

FIGS. 13A and 13B illustrate the Palmitoylation site in human tyrosinase.

FIGS. 14A-14D depict the effect of PP-2 and KA on melanin synthesis in NHEM.

FIG. 15 represents the effect of PP-2 and KA on human tyrosinase (DOPA oxidation) activity in vitro.

FIG. 16 depicts the effect of PP-2 on tyrosinase protein in NHEM.

DETAILED DESCRIPTION OF THE PREFERRED EMBODIMENTS OF THE INVENTION

Protein palmitoylation or S-acylation is a reversible post-translational lipid modification that affects the localization and activity of many proteins. As indicated schematically in FIG. 1, palmitoylation is an enzymatic process of attaching a palmitic acid group to a cysteine residue of a protein accomplished by a palmitoyl acyl transferase (PAT). PATs share a DHHC domain (aspartate-histidine-histidine-cysteine signature motif) and there are 23 or 24 separate DHHC-containing proteins in mammalian cells, each with its own substrate specificity. The consensus sequence for the target of the DHHC-containing proteins is not known, other than it contains a cysteine. Dozens of proteins are palmitoylated and the list is not yet complete. DHHC-containing proteins are mainly localized in the Golgi membrane where they cause relocation of target proteins by palmitoylation shortly after their synthesis.

Palmitoylation is enzymatically reversible by acyl-protein thioesterases (APTs) and palmitoyl-protein thioesterases (PPTs), which are ubiquitously located in the cytosol. There appear to be several APTs but only two PPTs in mammalian cells. Palmitoylated proteins are trafficked away from Golgi and attach to endosomes, lysozomes or plasma membranes. As a consequence of relocation they may be degraded (e.g. in lysozomes) or they can become substrates for PPT, change their localization and/or return to the Golgi for re-palmitoylation. In this way, the relative activity of a DHHC PAT and the APT/PPTs determine the localization of a protein, whether more concentrated near the Golgi or dispersed to endosome or plasma membrane. The system is dynamic, with proteins constantly shuttled back and forth and being degraded.

Inhibitors of Palmitoyl:protein thioesterase (PPT1) are described by Dawson et al. (Dawson, G., Schroeder, C., Dawson, P. Palmitoyl:protein thioesterase (PPT1) inhibitors can act as pharmacological chaperones in infantile Batten Disease. *Bioch. Biophys. Res. Comm.* 395:66-69, 2010.) Inhibitors with the N-terminal addition of the lipophilic fluorophore NBD, CS38 (NBD-αAGDap(Pal)VKIKK), was a 3-fold better inhibitor than Dap1 (AcGDap(Pal)VKIKK). CS38 was the most potent peptide inhibitor with an $IC_{50}$ of 2 μM. The NBD form of the authentic thiol (CS8: GGC(Pal) VKIKK) had comparable inhibitory activity to CS38. Additional peptides with TAT like polyarginine (R7) tails (AcGDap(Palm) GGR7) designed to promote cellular uptake, were also strong PPT1 inhibitors (for example AcGDap(Pal)GG)R)7). Any truncation of the VKIKK eliminated inhibitory activity. Inhibition of APTs is much less effective in blocking melanogenesis.

Virtually nothing is known about the role of palmitoylation in melanogenesis. In a genome-wide screen of genes that influence melanogenesis, the gene ZDHHC9 was identified as one in which inhibition by siRNA reduced melanogenesis (A. Ganesan, H. Ho, B. Bodemann, S. Petersen, J. Aruri, S. Koshy, Z. Richardson, L. Le, T. Krasieva, M. Roth, P. Farmer, M. White "Genome-wide siRNA functional genomics of pigmentation identifies novel genes and pathways that impact melanogenesis in human cells". PLOS Genetics 4(12): e1000298, doi:10.1371/journal.pgen.1000298, 2008). The siRNA to this PAT inhibited MITF (microthalmia-associated transcription factor) RNA and tyrosinase protein accumulation. The siRNA inhibition of tyrosinase protein was reversed by incubation with bafilomycin, which raises the pH of lysozomes and inhibits protein degradation. They suggest that their screening method identifies novel genes that impact melanosome trafficking/sorting of melanosome protein cargo. However, they imply that inhibition of palmitoylation should reduce melanogenesis. In fact, as uncovered in the present invention, general inhibition of palmitoylation increases melanogenesis, and PAT DHHC9 is not a specific modifier of tyrosinase.

Wu et al. studied palmitoylation of melanoregulin, a protein that, in its palmitoylated form, prevents the transfer of melanin from melanocytes to keratinocytes, (X. Wu, J. Martina, J. Hammer "Melanoregulin is stably targeted to the melanosome membrane by palmitoylation" *Bioch. Biophys. Res. Comm.* 426:209-214.) Palmitoylation localizes the melanoregulin protein to melanosomes thereby inhibiting the transfer of melanin from melanocytes. It was observed that inhibition of palmitoylation of melanoregulin reduces its accumulation at lysozomes and, by inference, at melanosomes. Wu et al. do not present any evidence regarding melanogenesis or tyrosinase.

The present invention resides in the surprising discovery by the inventors that palmitoylation/depalmitoylation of tyrosinase plays a role in melanogenesis. More specifically, the inventors have discovered that the palmitoylation of tyrosinase in melanocytes, by PATs (Palmitoyl-acyl transferases or DHHCs), leads to trafficking of tyrosinase away from melanosomes, resulting in a decrease in the appearance of melanin in skin and hair. The inventors theorize that the altered localization of tyrosinase away from the melanosome leads to its degradation. Furthermore, the inhibition of the palmitoylation of tyrosinase, that is, the inhibition of PATs, presumably results in the retention of tyrosinase in the melanosomes, and in the increased appearance of melanin in skin and hair. Compounds which inhibit PATs include 2-bromopalmitate (2-BP). As shown in the examples, below, the inventors have determined that the PATs responsible for the tyrosinase palmitoylation are DHHC 2, 3, 7 and 15, while DHHC 6, 11, 17, 21, and 22 show weak affinity, and DHHC 9 does not appear to palmitoylate tyrosinase. It was further ascertained that tyrosinase is palmitoylated on cysteine 500, since mutating this amino acid to alanine blocks palmitoylation of the enzyme.

The inventors have further discovered, as shown in the examples below, that inhibiting PPTs (palmitoyl-protein thioesterases), which are responsible for the de-palmitoylation of tyrosinase, leads to increased degradation of tyrosinase and a decrease in the appearance of melanin in skin and hair. PPTs are inhibited by palmitoylated peptides; that is, peptides containing a palmitoylated amino acid. Exemplary peptides useful for the purposes of the present invention include Palmitoylated peptide-1 or PP1 (Glyceryl Polymethacrylate (and) PEG-8 (and) Palmitoyl Oligopeptide, containing 100 ppm of the palmitoylated hexapeptide Palmitoyl-val-gly-val-ala-pro-glu), available as Biopeptide EL from Sederma, and Palmitoylated peptide-2 or PP2 (water (and) Butylene Glycol (and) Dextran (and) Palmitoyl Tripeptide-8, containing 500 ppm of a palmitoylated tri-peptide consisting of arginine, histidine, and phenylalanine), available as Neutrazen from Lucas Meyer Cosmetics.

The inhibitors of DHHC, PPT and/or APT may be used either alone or in combination with other inhibitors or promoters of pigmentation, such as hydroquinone, kojic acid and the like. These inhibitors can be combined with other cosmetically or dermatologically useful compounds such as sunscreens, anti-inflammatories, vitamin A and its derivatives, vitamin C and its derivatives and other vitamins, trace minerals and nutrients. The inhibitors can be mixed with common delivery forms for skin, such as emulsions, lotions, creams, serums, hydrogels, polymers, silicones, and the like. They can be combined with fragrances, anti-microbial compounds, preservatives and antioxidants.

EXAMPLES

Example 1

Effect of Palmitoylation Inhibitor 2-BP on Palmitoylation of Tyrosinase

Normal human epidermal melanocytes (NHEM) were incubated with 2-bromopalmitate (2-BP) for 24 hours, and total tyrosinase was determined by Western-blot (WB) using the mouse monoclonal anti-tyrosinase IgG antibody T311 (1:120 dilution). Total tyrosinase protein level was normalized by tubulin. Palmitoylated tyrosinase was evaluated by acyl-RAC and WB. The results shown in FIGS. 2A and 2B, are the average of three determinations SE. *$p<0.05$ vs. DMSO.

Incubation of NHEM with various concentrations of 2-BP, an inhibitor of palmitoylation, compared with a DMSO control, resulted in a statistically significant increase in the total amount of tyrosinase protein per cell. Additionally, while the amount of total protein increased, the amount of palmitoylated tyrosinase decreased.

Example 2

Effect of 2-BP on Melanin Synthesis in NHEM and Reconstructed Human Skin Model

NHEM were treated with indicated concentrations of 2-BP for 48 hours. Melanin content (closed bar) and cell number (open bar) were measured. Values are the average of three determinations±SE. *$p<0.05$ vs. DMSO. Macroscopic views of cell pellet were taken by digital camera (FIG. 3A). Reconstructed human skin models (Asian type) were incubated with 25 µM 2-BP for 17 days. Eumelanin (EM) and pheomelanin (PM) contents were determined and calculated by following formula. EM=PTCA*25, PM=4-AHP*9. Values are the average of three determinations±SE.*$p<0.05$ vs. DMSO. Macroscopic views of a human skin model after 17 days were taken by digital camera (FIG. 3B).

Incubation of NHEM with 2-BP at various concentrations, compared with a DMSO control, resulted in a statistically significant increase in melanin content per cell. Furthermore, incubating human skin models with 2-BP also resulted in a statistically significant increase in total melanin: eumelanin (EM) and pheomelanin (PM) content of the tissue.

Example 3

Effect of 2-BP on mRNA Expression and Glycosylation of Tyrosinase

NHEM were cultured with 2-BP for 6 or 24 hours. Tyrosinase mRNA levels were analyzed by real time quantitative PCR. The results shown are the average of three determinations±SE.*$p<0.05$ vs. DMSO (FIG. 4A). NHEM were incubated with 5 µM 2-BP for 24 hours. Glycosidase digestion treatment by endo H and WB analysis on mature and immature form of tyrosinase were conducted by WB (FIG. 4B). It was observed that incubation of NHEM with 2-BP resulted in a decrease of tyrosinase mRNA expression, but had no effect on the glycosylation of tyrosinase.

Example 4

Effect of 2-BP on Degradation of Tyrosinase

NHEM were treated with 1 µg/ml cycloheximide, protein synthesis inhibitor, and with (■) or without (◇) 10 µM 2-BP for 4 hours. Tyrosinase levels were analyzed by WB using the mouse monoclonal anti-tyrosinase IgG antibody T311 (1:120 dilution). The band intensities of tyrosinase were normalized by the band intensities of Glyceraldehyde 3-phosphate dehydrogenase (GAPDH) as internal control for each condition. The results shown are the average of three determinations±SE.*$p<0.05$ vs. DMSO (FIGS. 5A and 5B).

As shown in the figures, when NHEM are treated with cycloheximide, a protein synthesis inhibitor, tyrosinase levels are decreased. However, the additional presence of 2-BP in the incubation medium suppresses the effect of the cycloheximide, indicating that 2-BP suppresses the degradation of tyrosinase.

Example 5

Effect of 2-BP on Ubiquitination of Tyrosinase

NHEM were treated with 5 µM 2-BP for 24 hours. Equal protein amounts of cell lysate were used for IP by tyrosinase, and the ubiquitinated (UB) level of tyrosinase was analyzed by WB using anti-UB antibody.

The results, shown in FIG. 6 indicate that 2-BP has no effect on ubiquitination of tyrosinase. Thus, it was observed, as indicated in the schematic in FIG. 7, that while 2-BP suppresses tyrosinase degradation and results in activation of melanin synthesis, the ubiquitin proteasomal system does not participate in this phenomenon.

Example 6

Screening of Tyrosinase-Specific DHHC

As indicated hereinabove, PATs share a DHHC-rich domain and can be clustered into genetically conserved DHHC family proteins (Tsutsumi R, Fukata Y, Fukata M "Discovery of protein-palmitoylating enzymes", *Eur J Physiol*. 2008 September; 456(6):1199-206.). This is shown schematically in FIG. 8. To elucidate which of these DHHCs is involved in tyrosinase palmitoylation, HEK293T cells were transfected with tyrosinase and individual DHHCs. After metabolic labeling with [3H]palmitate, proteins were separated by SDS-PAGE (FIG. 9). The upper panel shows WB by anti-tyrosinase antibody; the lower panel shows an autoradiograph. DHHC 3, 7, 15 each show a strong effect, and DHHC 2, 6, 11, 17, 21, 22 each show a weak effect, on tyrosinase palmitoylation.

Example 7

Effect of DHHC 2, 3, 7, and 15 Silencing on Tyrosinase Palmitoylation in MNT-1 Cells To assess whether DHHC 2, 3, 7 and/or 15 participate in tyrosinase palmitoylation, the inventors assessed the effect of knocking down DHHC 2, 3, 7 or 15 on tyrosinase. MNT-1 cells were transfected with siRNA against DHHC 2, 3, 7 and 15 or control siRNA. After 3 days, siRNA transfection was repeated. At 6 days after the initial transfection, tyrosinase palmitoylation was analyzed by acyl-RAC and WB. The results (FIG. 10) show the average of six determinations±SE.*p<0.05 vs. DMSO. Results indicate that DHHC 2, 3, 7 and 15 may participate in tyrosinase palmitoylation. The reductions observed in the amounts of palmitoylated tyrosinase using siRNA to DHHC 2 and 15 are statistically significant.

Example 8

Analysis of the Intracellular Localizations of DHHC 2-, 3-, 7- and 15-Myc in NHEM NHEM (Asian) transfected with DHHC 2, 3, 7 and 15 with myc tags were stained with anti-myc antibody and also labeled with antibodies against Vtilb (Golgi body) or HMB45 (melanosome). Results are shown in FIGS. 11A and 11B. DHHC 2 was found to be localized in the melanosome, the plasma membrane, and in the Golgi body. Also found to be localized in the Golgi body were DHHC 7 and 15. DHHC 3 was found to be localized in the endoplasmic reticulum (ER).

Example 9

Palmitoylation Site in Human Tyrosinase

MNT-1 cells were transfected with a wild-type tyrosinase or one of three tyrosinases, mutated at one of three key cysteine codons, which resulted in the replacement of cysteine with alanine, as follows: C8A, C35A or C500A. After 48 hours, palmitoylation of tyrosinase was analyzed by acyl-RAC and WB. Results shown in FIG. 12A indicate that mutation in the codon for Cys500 results in a loss of tyrosinase palmitoylation, indicating that Cys500 is a palmitoylation site in human tyrosinase. Prediction of the most likely S-palmitoylation sites in human tyrosinase by software CSS-Palm 3.0, as shown in FIG. 12B, supports the finding.

Example 10

Palmitoylation Site in Human Tyrosinase

HEK293T cells were transfected with tyrosinase and individual DHHC. After 4 hour metabolic labeling with [3H] palmitate, proteins were separated by SDS-PAGE. In each of FIGS. 13A and 13B, the upper panel is an autoradiograph and the lower panel shows a WB analysis using anti-tyrosinase antibody. The results indicate that tyrosinase with mutation of C500A was not palmitoylated by DHHC 2, 3, 7 or 15 (white asterisks), further supporting the observation in Example 9, above, that the palmitoylation site of tyrosinase is Cys500.

Example 11

Effect of PP2 on Melanin Synthesis in NHEM

NHEM (Asian) were incubated for 120 hours in the presence of PP2, with or without 2-BP. PP2 inhibited melanin synthesis both in 2-BP-treated cells and in cells not treated with 2-BP without cytotoxicity (FIGS. 14A and 14B). Mean±S.E. (N=3)*p<0.05, vs. control.

Kojic Acid (KA) was used as a positive control. As shown in FIGS. 14C and 14D, KA mildly inhibited melanin synthesis both in 2-BP treated cells and cells not treated with 2-BP.

Example 12

Mechanism of Action of PP2 on Melanogenesis: Effect of PP2 on Melanin Synthesis in NHEM As shown in FIG. 15, PP2 did not inhibit human tyrosinase (DOPA oxidation) activity in vitro, while Kojic acid (positive control) inhibited tyrosinase activity in a dose dependent manner. Mean±S.E. (N=4)*p<0.05, vs. control.

Example 13

Mechanism of Action of PP2 on Melanogenesis: Effect of PP2 on Tyrosinase Protein Level in NHEM NHEM were incubated for 48 hours in the presence of PP2 with or without 2-BP. As shown in FIG. 16, PP2 decreased tyrosinase protein level in 2-BP-treated human NHEM (Asian). Mean±S.E. (N=3)*p<0.05, vs. control.

While the present invention has been described hereinabove with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the present invention.

What we claim is:

1. A method for increasing the appearance of melanin in mammalian skin or hair in need of such increase, comprising treating the skin or hair with a melanin-increasing effective amount of at least one inhibitor of an aspartate-histidine-histidine-cysteine domain (DHHC) selected from the group consisting of DHHC 2, 3, 7, 15, 6, 11, 17, 21, or 22.

2. The method of claim 1 wherein the at least one inhibitor is 2-bromopalmitate (2-BP).

3. The method of claim 1 comprising treating the skin or hair with a composition comprising a melanin increasing-effective amount of at least one inhibitor of DHHC 2, 3, 7, 15, 6, 11, 17, 21, or 22, in combination with a further melanin-increasing ingredient.

* * * * *